United States Patent [19]
Keil

[11] Patent Number: 4,532,132
[45] Date of Patent: Jul. 30, 1985

[54] SKIN CARE FORMULATIONS COMPRISING A WATER-IN-MINERAL OIL EMULSION AND SILOXANE COMPOSITIONS THEREFOR

[75] Inventor: Joseph W. Keil, Midland, Mich.

[73] Assignee: Dow Corning Corporation, Midland, Mich.

[21] Appl. No.: 484,002

[22] Filed: Apr. 11, 1983

[51] Int. Cl.$^3$ .............................. C07F 7/08; C07F 7/18
[52] U.S. Cl. .................................. 514/772; 556/446; 514/937
[58] Field of Search ........................ 556/446; 424/184

[56] References Cited

U.S. PATENT DOCUMENTS

| Re. 25,727 | 2/1965 | Haluska | 556/445 |
|---|---|---|---|
| 2,917,480 | 12/1959 | Bailey et al. | 556/446 X |
| 3,234,252 | 2/1966 | Pater | 556/416 |
| 3,272,762 | 9/1966 | Ibbotson et al. | 556/446 X |
| 3,299,113 | 1/1967 | Haluska | 556/446 |
| 3,480,583 | 11/1969 | Bailey et al. | 556/446 |
| 3,526,651 | 9/1970 | Rossmy et al. | 556/446 |
| 3,657,305 | 4/1972 | Morehouse | 556/445 |
| 3,686,254 | 8/1972 | Morehouse | 556/445 |
| 3,980,688 | 9/1976 | Litteral et al. | 556/446 |
| 4,047,958 | 9/1977 | Yoneyama et al. | 556/445 |
| 4,151,304 | 4/1979 | Evans | 514/777 |
| 4,269,992 | 5/1981 | Litteral et al. | 556/446 |
| 4,311,695 | 1/1982 | Starch | 514/63 |
| 4,381,241 | 4/1983 | Romenesko et al. | 514/771 |

FOREIGN PATENT DOCUMENTS 1041341  1/1963  United Kingdom .
1221156  7/1969  United Kingdom .

Primary Examiner—Paul F. Shaver
Attorney, Agent, or Firm—George A. Grindahl

[57] ABSTRACT

Organopolysiloxane-polyoxyalkylene block copolymers having a limited number of dimethylsiloxane units, at least one 6 to 16 carbon alkyl radical and at least one polyoxyalkylene radical are good emulsifiers for preparing water-in-mineral oil emulsions if the polyoxyalkylene radicals do not account for more than $\frac{1}{3}$ of the molecular weight of the block copolymer. The block copolymers are readily dispersible or dissolvable in mineral oil to which a personal care component can be added. Personal care emulsion compositions can then be prepared by emulsifying an aqueous phase into the mineral oil phase.

23 Claims, No Drawings

SKIN CARE FORMULATIONS COMPRISING A WATER-IN-MINERAL OIL EMULSION AND SILOXANE COMPOSITIONS THEREFOR

BACKGROUND OF THE INVENTION

The present invention relates to organopolysiloxane emulsifiers, and mineral oil solutions thereof, which are useful for preparing aqueous skin care emulsions and to skin care emulsions comprising said organopolysiloxane emulsifiers and a water-containing phase dispersed in a mineral oil-containing phase.

Skin care emulsions comprising water and mineral oil are valuable compositions because of the well known salutary skin-moisturizing and skin-softening effects that are obtained when such emulsions are applied to the skin. Of course, skin care emulsions typically further comprise other components, such as odorants; efficacious components, such as emollients, humectants, barrier agents and healing agents; and stabilizing agents, such as emulsifiers and preservatives to enhance the efficacy and customer acceptance of said emulsions.

Skin care emulsions comprising water and mineral oil are typically oil-in-water type emulsions instead of water-in-oil type emulsions, a situation which is at least partially due to a relative abundance of cosmetically acceptable emulsifiers for the former type and a relative shortage of cosmetically acceptable emulsifiers for the latter type.

However, water-in-mineral oil skin care emulsions are highly desirable because of the pleasant dry feel that one receives when such an emulsion is applied to one's skin, an effect not available from oil-in-water emulsions. Furthermore, since water-in-oil emulsions are not readily miscible with water they are valued as water-resistant skin care compositions. At least for these reasons, considerable effort has been devoted to the search for new emulsifiers that will provide water-in-mineral oil emulsions.

Starch, U.S. Pat. No. 4,311,695, discloses personal care creams and lotions of the water-in-oil type wherein the oil comprises a volatile component and a personal care component dissolved therein. Mineral oil is disclosed by Starch as a suitable personal care component. However, because of the particular organopolysiloxane emulsifier that is used by Starch the personal care composition must contain a water-soluble alcohol such as ethanol, isopropanol, propylene glycol or glycerol. The emulsifier that is used by Starch is an organopolysiloxane-polyoxyalkylene block copolymer wherein at least 95 percent of the organic radicals in the organopolysiloxane block are the methyl radical and the balance are ethyl, vinyl, phenyl and an alkylene radical linking the polyoxyalkylene block to the organopolysiloxane block, and the weight ratio of organosiloxane blocks to polyoxyalkylene blocks is equal to from 2/1 to 8/1.

U.K. Pat. No. 1,221,156 discloses a water-in-oil ointment base wherein the oil is an organosiloxane-oxyalkylene block copolymer and further teaches the desirability of bonding the oxyalkylene block of the block copolymer to the organosiloxane block by way of a hydrolytically stable silicon-carbon bond. Although the ointment base can further comprise adjuvants such as a scent, a pigment, a filler or white petroleum jelly, compositions comprising mineral oil or a water-in-mineral oil emulsion are not contemplated therein. The organopolysiloxane-oxyalkylene block copolymer recited in this patent contains only methyl radicals and alkylene-linked oxyalkylene radicals with the latter accounting for from 10 to 35 percent by weight of the block copolymers.

U.K. Pat. No. 1,041,341 relates to water-hydrocarbon systems which can be either oil-in-water emulsion systems or water-in-oil emulsion systems, depending upon which component is the major component. The emulsifier that is used in these systems is an organopolysiloxane-polyoxyalkylene block copolymer wherein the polyoxyalkylene blocks account for from 50 to 95 percent by weight of the block copolymer.

It is evident to one having knowledge of the skin care formulation art and of the emulsions art that there is a paucity of emulsifiers that are suitable for forming water-in-mineral oil emulsions that demonstrate stability to separation.

Although the above-noted patents relate to water-in-oil emulsion compositions their failure to disclose water-in-mineral oil compositions is understandable in view of the present invention. That is to say, the organopolysiloxane-oxyalkylene emulsifiers that are used in compositions of the above-noted references are ineffective to emulsify water-in-mineral oil because they contain excessive oxyalkylene portions and/or excessive methylsiloxane portions, unlike the organopolysiloxanes of the present invention.

BRIEF SUMMARY OF THE INVENTION

It is an object of the present invention to provide skin care emulsion compositions which comprise a water-containing phase dispersed in a mineral oil-containing phase. It is a further object of this invention to provide organopolysiloxane emulsifiers and mineral oil solutions thereof, which are effective for emulsifying water, containing an emulsion-stabilizing amount of a cosmetically acceptable electrolyte, in mineral oil or a mineral oil-containing oil phase.

These objects, and others which will become apparent to one skilled in the organosilicone art and/or the skin care formulation art upon considering the following disclosure and appended claims, are obtained by preparing an organopolysiloxane-polyoxyalkylene block copolymer having a limited number of dimethylsiloxane units, at least one silicon-bonded alkyl radical having from 6 to 16 carbon atoms and at least one polyoxyalkylene radical containing a majority of oxyethylene units, wherein the polyoxyalkylene radicals do not account for more than ⅓ of the molecular weight of the block copolymer. The resulting block copolymer is readily soluble in mineral oil and mineral oil-containing mixtures and is able to emulsify large amounts of water in mineral oil. An emulsion-stabilizing amount of a cosmetically acceptable electrolyte is included in the water.

DETAILED DESCRIPTION OF THE INVENTION

The present invention has three aspects. In a first aspect the present invention relates to an organopolysiloxane having the formula

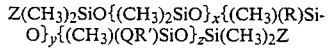

wherein QR' denotes a polyoxyalkylene radical consisting of a Q portion having the formula —(OCH$_2$CH$_2$)$_p$(OCHCH$_3$CH$_2$)$_q$OR" and an R' portion linking the Q portion to a silicon atom, R denotes an alkyl radical having from 6 to 16 carbon atoms, R' denotes an alkylene linking radical, R" denotes a hydrogen atom or a lower alkyl radical, Z denotes a monovalent radical selected from the group consisting of hydrocarbon radicals having from 1 to 5 carbon atoms, QR'— radicals and R radicals, there being an average of at least one QR'— radical and an average of at least one R radical per molecule of organopolysiloxane composition and the average values of x, y, z, p and q being such that p q, p+q has a value sufficient to provide a radical weight for Q of from 600 to 3500, x 3y, x+y+z has a value of from 30 to 400 and the total weight of Q radicals in the organopolysiloxane does not exceed a value of about ⅓ of the total weight of the organopolysiloxane.

The organopolysiloxanes of the present invention are substantially linear polydiorganosiloxanes which are terminated with triorganosiloxane units having the formula Z(CH$_3$)$_2$SiO$_½$ wherein Z denotes an R radical or a QR'— radical, each delineated below, or a monovalent hydrocarbon radical having from 1 to 5 carbon atoms, such as methyl, ethyl, propyl, isopropyl, butyl, pentyl and vinyl. Each Z preferably denotes a methyl radical because the trimethylsiloxy unit is a readily preparable siloxane unit.

The organopolysiloxanes of this invention must demonstrate a preference for, such as a solubility or near-solubility in, mineral oil while at the same time be able to stabilize a dispersed aqueous phase. Therefore the following requirements must be met.

In the above formula for the organopolysiloxanes of this invention the average values of x, y and z are such that the value of x is equal to or less than the value of 3y, the sum of the values of x, y and z has a value of from 30 to 400 and R and Q radicals are always present but the total weight of hydrophilic Q radicals in the organopolysiloxane does not exceed a value of about ⅓ of the total weight of the organopolysiloxane. In other words, in order for the organopolysiloxane to be effective as an emulsifier for water-in-mineral oil emulsions the organopolysiloxane should be composed of at least ⅔ by weight of a oleophilic portion; but, said oleophilic portion should consist of less than about 75 mol percent (CH$_3$)$_2$SiO$_{2/2}$ units and more than about 25 mol percent (CH$_3$)(R)SiO$_{2/2}$ units; excluding the terminal Z(CH$_3$)$_2$SiO$_½$ siloxane units and the Q-bonding (CH$_3$)(—R')SiO$_{2/2}$ siloxane units.

For example, an organopolysiloxane of this invention having the formula

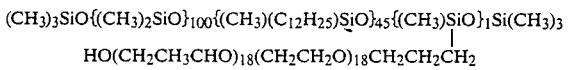
HO(CH$_2$CH$_3$CHO)$_{18}$(CH$_2$CH$_2$O)$_{18}$CH$_2$CH$_2$CH$_2$ has a total molecular weight of 19815 and the hydrophilic portion of the organopolysiloxane (Q) has a weight of 1855 or 9.4 percent by weight. The oleophilic portion of the organopolysiloxane has a weight of 17960 and is 69 mol percent dimethylsiloxane units and 31 mol percent methyldodecylsiloxane units, neglecting trimethylsiloxy end groups and the (CH$_3$)(—CH$_2$CH$_2$CH$_2$)SiO$_{2/2}$ siloxane unit.

Within the limits for the values of x, y and z, noted above, x preferably has a value of from 0 to 100. Within this preferred range of values two classes of organopolysiloxanes are distinct. In a highly preferred class x has a value of zero; i.e., the organopolysiloxanes are free of dimethylsiloxane units. This class of organopolysiloxanes is highly preferred because the members thereof are more effective than others as emulsifiers for the emulsion compositions of this invention, delineated below. In another preferred class of organopolysiloxanes x has a value of from 1 to about 100, with the proviso that it does not have a value greater than the value of 3y. These organopolysiloxanes have a sufficiently small amount of dimethylsiloxane units that their viscosities do not become excessively high for their large scale preparation.

Within the limits for x, y and z, noted above, including the preferred limits for x, the sum of y+z preferably has a value of from about 30 to about 70. One reason for limiting the value of y+z as stated is to facilitate its preparation, as delineated below. Another reason for so limiting the value of y+z is to provide an organopolysiloxane which has sufficient surface active characteristics and a low enough molecular weight to be easily soluble in mineral oil.

Within the limits for x, y and z, noted above, including the preferred limits for x and y+z, z preferably has a value of from about 1 to about 3, and most preferably no more than about 2. When the average value of z lies outside of these limits the resulting emulsion compositions of this invention, delineated below, have less-than-optimum stability to separation.

It is to be noted that the values of x, y and z are average values, their various actual values being determined by the random process by which each individual organopolysiloxane molecule is prepared.

The oganopolysiloxanes of the present invention contain at least one siloxane unit having the formula (CH$_3$)(R)SiO$_{2/2}$ or R(CH$_3$)$_2$SiO$_½$ wherein R denotes an alkyl radical having from 6 to 16 carbon atoms. When R has less than 6 carbon atoms the solubility of the resultant organopolysiloxane in mineral oil is less than desired and there is also the undesirable necessity of using extremely volatile olefins when preparing the organopolysiloxanes. When R has more than 16 carbon atoms the resulting organopolysiloxanes do not provide satisfactory water-in-mineral oil emulsions, which are another aspect of this invention.

Examples of suitable R radicals for the purposes of this invention include normal alkyl radicals such as hexyl, heptyl, octyl, nonyl, decyl, dodecyl, tetradecyl and hexadecyl and branched alkyl radicals such as iso-octyl, secondary octyl, 2-ethylhexyl, secondary dodecyl and isododecyl. When there is more than one R radical present in the organopolysiloxanes of this invention they can all be the same radical or two or more different radicals, such as two or more different dodecyl radicals or two or more radicals having a differing number of carbon atoms or two or more radicals differing in the number of carbon atoms and in structure.

R is preferably the dodecyl radical because the corresponding organopolysiloxanes of this invention possess a plurality of favorable properties, including ease of synthesis (relatively non-volatile olefins are used), good solubility in mineral oil and desirable handling viscosity (they are liquids, not waxes). However, although dodecyl radicals are preferred as the R radicals, the radicals having from 10 to 14 carbon atoms, both inclusive, provide one or more of the favorable properties noted above and the preferred choice of R may depend on the consideration of other factors such as the purity, cost and/or availability of the corresponding olefin precursor.

The organopolysiloxanes of the present invention, in addition to containing at least one siloxane unit having the formula $(CH_3)(R)SiO_{2/2}$ or $R(CH_3)_2SiO_{\frac{1}{2}}$, further contain at least one siloxane unit having the formula $(CH_3)(QR')SiO_{2/2}$ or $(QR')(CH_3)_2SiO_{\frac{1}{2}}$, wherein QR' denotes a polyoxyalkylene radical.

In the polyoxyalkylene radical, QR', Q denotes a hydrophilic radical having the formula $-(OCH_2CH_2)_p(OCHCH_3CH_2)_qOR''$ wherein R'' denotes a hydrolytically stable terminating radical, such as the hydrogen atom or a lower alkyl radical, such as methyl, ethyl, isopropyl or butyl. Preferably R'' denotes the hydrogen atom to further enhance the hydrophilic nature of the Q radical.

In the above formula for Q, p and q denote numbers whose values are such that the number of oxyethylene units ($OCH_2CH_2$) is, on average, equal to or greater than the number of oxypropylene units ($OCHCH_3CH_2$) therein, and the weight of the Q radical (radical weight) has a value of from about 600 to about 3500. Organopolysiloxanes of this invention wherein the Q radicals thereof have substantially more oxypropylene units than oxyethylene units are not expected to have suitable emulsifying properties for the purposes of this invention. Examples of typical values of p and q which are suitable in the organopolysiloxanes of this invention include, but are not limited to, $p=15$, $q=0$; $p=18$, $q=18$; $p=25$, $q=25$; and $p=29$, $q=7$. It is to be noted that the values of p and q are average values, the actual values of p and q having various values which are determined by the random process by which each individual polyoxyalkylene radical precursor is prepared.

In the polyoxyalkylene radical, QR', R' denotes an alkylene radical which serves to join the Q radical to a silicon atom by a silicon carbon bond. R' is preferably the propylene radical because the preferred precursor allyl-initiated polyoxyalkylenes are most readily prepared. However, the identity of R' is not critical and may be any alkylene radical such as methylene, ethylene, propylene, butylene or higher alkylene.

A highly preferred QR'— radical for the purposes of this invention has the formula

—$CH_2CH_2CH_2(OCH_2CH_2)_p(OCHCH_3CH_2)_qOH$ wherein the values of p and q are as delineated above and, preferably, where the values of p and q are as exemplified above.

The organopolysiloxanes of this invention can be prepared by any suitable method; however, the preferred method comprises the hydrosilylation reaction of an olefin and an olefinically substituted polyoxyalkylene with a suitable polymethylhydrogensiloxane in the presence of a noble metal catalyst, in the well known manner. Examples of suitable polymethylhydrogensiloxanes include $HMe_2SiO(MeHSiO)_{y+z}SiMe_2H$, $Me_3SiO(MeHSiO)_{y+z}SiMe_3$, $Me_3SiO(Me_2SiO)_x(MeHSiO)_{y+z}SiMe_3$ and $HMe_2SiO(Me_2SiO)_x(MeHSiO)_{y+z}SiMe_2H$ wherein Me denotes the methyl radical. Preferably the olefin is allowed to react with the polymethylhydrogensiloxane first, followed by the olefinically substituted polyoxyalkylene. For example, to obtain the most preferred organopolysiloxanes of this invention a suitable amount of dodecene is reacted with $Me_3SiO(MeHSiO)_{30 \, to \, 70}SiMe_2$ to form an alkylated siloxane, followed by a reaction of $CH_2=CHCH_2(OCH_2CH_2)_p(OCHCH_3CH_2)_qOH$ with the alkylated siloxane in the presence of a suitable solvent such as isopropanol. When the organopolysiloxane of this invention is to contain from 1 to 3 QR'— radicals it is preferred that from 80 to 95 percent of the stoichiometric amount of olefin be reacted with the polymethylhydrogensiloxane to provide a partially alkylated polymethylhydrogensiloxane and the balance of the olefin or an excess thereof, be reacted after the olefinically substituted polyoxyalkylene has been reacted with the thus partially alkylated polymethylhydrogensiloxane.

When the composition of the three aspects of this invention can further contain a non-volatile alcohol, such as isostearyl alcohol, the organopolysiloxanes of this invention are preferably prepared by the method of Brown, claimed in a copending application entitled "Organopolysiloxane Emulsifier Compositions and Method Therefor" which has been assigned to the assignee of this invention. Briefly said method of Brown comprises reacting the olefinically substituted polyoxyalkylene with an organohydrogenpolysiloxane in the presence of a higher aliphatic alcohol as a solvent.

The organopolysiloxanes of this invention can further comprise trace amounts of silicon-bonded radicals which occur as impurities in, or arise during the preparation of, commercial organopolysiloxanes. Examples of such silicon-bonded radicals include hydrogen atoms, hydroxyl radicals, alkoxy radicals, etc.

The organopolysiloxanes of this invention can further comprise up to about 10 percent by weight of unreacted starting materials, and their associated impurities, that are used in the preparation thereof. Examples of such unreacted starting materials and their associated impurities include hydrocarbons, such as alkanes and alkenes; polyoxyalkylenes, such as polyoxyalkylene glycols and olefinically substituted polyoxyalkylenes; solvents such as isopropanol, higher aliphatic alcohols and toluene; and unreacted siloxanes, such as polydimethylsiloxanes, cyclopolydimethylsiloxanes and hexamethyldisiloxane.

As indicated above, the organopolysiloxanes of this invention find utility as emulsifiers for water-in-mineral oil compositions, optionally further comprising other components, which are useful as skin-care compositions.

In a second aspect the present invention relates to a homogeneous composition comprising (A) an organopolysiloxane have the formula $Z(CH_3)_2SiO\{(CH_3)_2SiO\}_x\{(CH_3)(R)SiO\}_y\{(CH_3)(QR')SiO\}_zSi(CH_3)_2Z$ wherein QR' denotes a polyoxyalkylene radical consisting of a Q portion having the formula $-(OCH_2CH_2)_p(OCHCH_3CH_2)_qOR''$ and an R' portion linking the Q portion to a silicon atom, R denotes an alkyl radical having from 6 to 16 carbon atoms, R' denotes an alkylene linking radical, R'' denotes a hydrogen atom or a lower alkyl radical, Z denotes a monovalent radical selected from the group consisting of hydrocarbon radicals having from 1 to 5 carbon atoms, QR'— radicals and R radicals, there being an average of at least one QR'— radical and an average of at least one R radical per molecule of organopolysiloxane and the average values of x, y, z, p and q being such that $p \geq q$, $p+q$, has a value sufficient to provide a radical weight for Q of from 600 to 3500, $x \leq 3y$, $x+y+z$ has a value of from 30 to 400 and the total weight of Q radicals in the organopolysiloxane does not exceed a value of about ⅓ of the total weight of the organopolysiloxane, and (B) mineral oil.

The compositions of the second aspect of this invention constitute a valuable form of this invention, especially with respect to the handling convenience for the user thereof. The organopolysiloxanes of the first aspect of this invention are frequently viscous liquids, and sometimes waxes, that are difficult to handle on a large scale. The present invention therefore provides a composition which has an improved handling viscosity and which can be readily used, without heating to facilitate handling, as for example in the preparation of water-in-mineral oil emulsions.

Component (A) of the compositions of the second aspect of this invention is an organopolysiloxane of the first aspect of this invention, including the preferred embodiments thereof, that are properly delineated above.

Component (B) of the compositions of the second aspect of this invention is mineral oil. Mineral oils which are suitable for the purposes of this invention are well known in the skin care formulation art and need no further delineation herein. The viscosity of the mineral oil that is used in this, and the third, aspect of this invention, preferably has a value of less than 100 centistokes at 25° C.

The relative amounts of components (A) and (B) in the compositions of the second aspect of this invention are not narrowly critical, it being necessary only that the composition be a homogeneous composition, such as a solution or a stable dispersion or emulsion which has an improved handling viscosity. For example, the weight ratio of component (A) to component (B) can be substantially the same as the weight ratio of the same components as they occur in the emulsion compositions of this invention, delineated below. Of course, relatively smaller or larger amounts of component (A) are possible, and may even be preferred. For example, a composition of the second aspect of this invention having an amount of organopolysiloxane which is beyond what is desired to prepare an emulsion composition therefrom, such as an equal weight mixture of components (A) and (B), is nevertheless of value because it is easily handled and is easily diluted to the desired concentration for emulsion preparation by the simple admixing of additional mineral oil therewith.

The compositions of the second aspect of this invention can further comprise small amounts of components which are incidental to the preparation of the organopolysiloxane component thereof, noted above in the detailed description of the first aspect of this invention. In particular, when the organopolysiloxane component is prepared by the preferred method of Brown comprising the use of a non-volatile alcohol, noted above, the compositions of the second aspect of this invention will also comprise the non-volatile alcohol.

The compositions of the second aspect of the present invention can be prepared by any suitable method; however, they are preferably prepared by simply admixing the organopolysiloxane component, with mineral oil in the desired amounts until a homogeneous mixture is obtained. In certain cases it may be advantageous to heat the organopolysiloxane component and/or the mineral oil moderately to facilitate said admixing.

The compositions of the second aspect of this invention are particularly useful for preparing the emulsion compositions of this invention, delineated below. For example, a composition of the second aspect of this invention consisting of no more than about one part by weight of organopolysiloxane component (A) for every one part by weight of mineral oil can be prepared and, optionally, transported and/or stored before being diluted with additional mineral oil, if necessary, and used as a base fluid for the preparation of a skin care composition of this invention delineated below.

In a third aspect the present invention relates to an emulsion composition comprising (I) a dispersed phase comprising water and a cosmetically acceptable electrolyte dissolved therein, (II) a cosmetically acceptable continuous phase comprising mineral oil, and (III) an organopolysiloxane having the formula

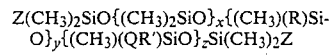

$$Z(CH_3)_2SiO\{(CH_3)_2SiO\}_x\{(CH_3)(R)SiO\}_y\{(CH_3)(QR')SiO\}_zSi(CH_3)_2Z$$

wherein QR' denotes a polyoxyalkylene radical consisting of a Q portion having the formula $-(OCH_2CH_2)_p(OCHCH_3CH_2)_qOR''$ and an R' portion linking the Q portion to a silicon atom, R denotes an alkyl radical having from 6 to 16 carbon atoms, R' denotes an alkylene linking radical, R'' denotes a hydrogen atom or a lower alkyl radical, Z denotes a monovalent radical selected from the group consisting of hydrocarbon radicals having from 1 to 5 carbon atoms, QR'— radicals and R radicals, there being an average of at least one QR'— radical and an average of at least one R radical per molecule of organopolysiloxane and the average values of x, y, z, p and q being such that p≧q, p+q has a value sufficient to provide a radical weight for Q of from 600 to 3500, x≦3y, x+y+z has a value of from 30 to 400 and the total weight of Q radicals in the organopolysiloxane does not exceed a value of about ⅓ of the total weight of the organopolysiloxane.

The emulsion compositions which form the third aspect of the present invention are of the water-in-oil type wherein the dispersed phase is water further comprising a small amount of a cosmetically acceptable electrolyte and the continuous phase is an oil comprising mineral oil. The principal purpose of the electrolyte is to provide long term stability against separation for the emulsion. This is particularly desirable when the emulsion compositions of this invention are formulated as flowable compositions, such as lotions, which do not derive any substantial stability to separation from high viscosity as do cream formulations.

The amount of cosmetically acceptable electrolyte that is present in the emulsion compositions of this invention is merely that amount that will provide the desired long term, for example 18 months, stability. Typically long term stabilization against separation can be achieved with as little as 0.5 percent by weight, based on the weight of water, of an electrolyte and more than this amount is unnecessary. In some instances as much as 3 percent by weight of an electrolyte provides optimum stability.

Cosmetically acceptable electrolytes are well known in the cosmetic art, including the skin-care formulation art, and need no extensive delineation herein. Typical examples thereof include sodium chloride, sodium acetate, sodium citrate, sodium sulfate, lime, sodium phosphate, calcium chloride, ammonium carbonate and magnesium sulfate.

The continuous phase, component (II), of the emulsion compositions of this invention is a cosmetically acceptable oil which comprises the mineral oil, including preferred viscosities thereof, herein above delineated. The continuous phase can consist solely of mineral oil as the skin care component, or it can further comprise up to 5 parts by weight of one or more additional skin care components for every 1 part of mineral oil.

In addition to mineral oil, further examples of skin care components that are suitable in the emulsion compositions of this invention include other emollients, such as hydrocarbon oils and waxes such as petrolatum, perhydrosqualene and paraffin wax; silicone oils such as cyclic and/or linear polydimethylsiloxanes, polyphenylmethylsiloxanes, methylsiloxane resins and mixtures thereof; esters, such as lanolin, spermaceti, triglyceride esters, fatty esters of glycols, glycerol, sorbitol and mannitol, alkyl esters of fatty acids such as methyl esters of fatty acids; non-volatile alcohols, such cholesterol, lanolin alcohol, lauryl alcohol, cetyl alcohol, oleyl alcohol and stearyl alcohol; phospholipids; fatty alcohol ethers, such as stearyl ether of polyoxyethylene; and hydrophilic derivatives of said other emollients.

The emulsion compositions of this invention can further comprise other skin care components which are typically used in skin care compositions, in either the aqueous phase or the mineral oil phase such as barrier agents, healing agents, humectants, preservatives, perfumes, colorants, sun screens, vitamins, hormones, fillers and cosurfactants.

Component (III) of the emulsion compositions of this invention is an organopolysiloxane of this invention, including preferred embodiments thereof, that are properly delinated above.

The emulsion compositions of this invention can comprise from about 1 to about 80, preferably from about 50 to about 80 parts by weight of dispersed phase; from about 5 to about 40, preferably from 10 to 30 parts by weight of continuous phase and from about 0.2 to about 10, preferably from about 1 to about 3 parts by weight of a organopolysiloxane emulsifier, component (III); the total of dispersed phase, continuous phase and organopolysiloxane emulsifier being 100 parts by weight.

Although not required the emulsion compositions of this invention can further contain one or more silicon-free surfactants which have an H.L.B. rating of up to 10. Examples of suitable silicon-free surfactants can be found in well known publications such as McCutcheon's "Detergents and Emulsifiers", Allured Publishing Company, Ridgewood, NJ, which is hereby incorporated by reference to disclose surfactants having an H.L.B. value of up to 10.

The form of the compositions of this invention can range from freely flowing lotions to stiff creams to solidified gels, the exact form being largely, but not exclusively, determined by the ratio of aqueous phase to oil phase present therein in the well known manner.

The emulsion compositions of this invention can be prepared in any suitable manner; however, they are typically prepared by admixing, in the presence of the organopolysiloxane emulsifier, a previously prepared aqueous phase with a previously prepared oil phase, in the well known manner, using sufficient agitation and/or shear to disperse the aqueous phase as droplets having a size of less than 10 micrometers, preferably less than 1 micrometer. Mild heating of the components can be used, if desired, to aid in the admixing.

Of course the skin care emulsion compositions of the present invention can be packaged for the ultimate user in the well known ways such as in collapsible tube, squeeze bottle, jar, aerosol, roll-on, impregnated pad and unit dose packages.

The compositions of the prsent invention are further illustrated, but not limited, by the following examples. All parts and percentages are by weight unless otherwise stated. Me denotes the methyl radical and Ph denotes the phenyl radical. Viscosities were measured at 25° C.

Emulsifier Preparation—The organopolysiloxanes of this invention were typically prepared by (1) reacting a siloxane fluid containing a plurality of methylhydrogensiloxane units with an alpha olefin in the presence of a platinum-containing hydrosilylation catalyst to replace a majority of the silicon-bonded hydrogen atoms with alkyl groups; followed by (2) reacting the remaining silicon-bonded hydrogen atoms of the resulting alkylated methylsiloxane with an olefin-endblocked polyoxyalkylene in the presence of isopropyl alcohol, which was thereafter removed from the final reaction product. In a variation of this typical preparation a major portion of the alpha olefin was reacted in Step 1 and the remaining portion of the alpha olefin was reacted after Step 2 had been completed. In another variation the isopropyl alcohol was omitted and isostearyl alcohol was used as a solvent and was allowed to remain with the final reaction product.

EXAMPLE 1

The following preparation of Emulsifier No. 1 (Table I) is illustrative of the typical method of organopolysiloxane preparation.

A mixture of 607.5 parts (0.15 mols) of $Me_3SiO(MeHSiO)_{65}SiMe_3$ and 0.38 parts of a 0.1N solution of $H_2PtCl_6.6H_2O$ in isopropyl alcohol was placed under a $N_2$ atmosphere and heated to 90° C. With the heat turned off 1077 parts (9.6 mols) of 1-octene was slowly added to the mixture at such a rate as to control the exotherm and keep the reaction temperature below 120° C. When the addition of 1-octene had been completed a mixture of 525 parts of isopropyl alcohol, 420 parts (0.16 mols = 10% excess) of $CH_2=CHCH_2(OCH_2CH_2)_{24.4}(OCHCH_3CH_2)_{24.4}OH$ and 0.38 parts of the platinum-containing catalyst solution was added to the reaction mixture, the heat was turned on and the reaction mixture was refluxed for 2 hours. The isopropyl alcohol was then removed by distillation at reduced pressure. The clear amber-colored liquid had a viscosity of 88,000 centipoise. Emulsifier Nos. 2 to 15 were prepared in a similar manner, the particular process varying only in the amount of time that the isopropanol-containing reaction mixture was refluxed (from 1 to 3 hours) and in the particular alpha olefin and olefinically substituted polyoxyalkylene that were used.

EXAMPLE 2

The following preparation of Emulsifier No. 16 (Table I) is illustrative of the method of Brown disclosed in a copending application entitled, "Organopolysiloxne Emulsifier Compositions and Method Therefor" which has been assigned to the assignee of this invention and which is incorporated herein by reference.

A mixture of 40 parts of $Me_3SiO(MeHSiO)_{40}SiMe_3$ and 0.3 parts of a 0.5% solution of $H_2PtCl_6.6H_2O$ in isopropanol was placed under a nitrogen atmosphere and heated to 85° C. Approximately 92 parts of dodecene having an olefinic activity of 91% were slowly added to the above mixture so that the temperature of the reaction mixture did not exceed 140° C. Isostearyl alcohol, 20.75 parts, was then added to the reaction mixture along with another 0.33 part portion of the platinum-containing solution. Forty parts of $CH_2=CHCH_2(OCH_2CH_2)_{19}(OCHCH_3CH_2)_{19}OH$ were then added to the reaction mixture and the resulting mixture was heated at 140° C. for 45 minutes. Another 0.33 part portion of platinum-containing solution and 38 parts of the 91% active dodecene were then added and the resulting mixture was heated for 1 hour at 140° C. and then cooled to room temperature under the nitrogen atmosphere. The resulting organopolysiloxane had a viscosity of 3130 centistokes.

EXAMPLE 3

This example illustrates the preparation of Emulsifier No. 19 that is shown in Table II.

A mixture of 2082 parts of an organohydrogenpolysiloxane having the formula $Me_3SiO(Me_2SiO)_{100}(MeHSiO)_{47.5}SiMe_3$ and 1 part of a 0.1N solution of $H_2PtCl_6.6H_2O$ in isopropanol was placed under a nitrogen purge and heated to 80° C. Dodecene, 1566 parts, was added to the warm mixture at such a rate (40 minutes) that the exothermic reaction did not raise the reaction mixture temperature above 110° C. The reaction mixture was then cooled to 70° C. and a mixture of 1050 parts of isopropanol, 560 parts of $CH_2=CHCH_2(OCH_2CH_2)_{24.4}(OCHCH_3CH_2)_{24.4}OH$ and 1 part of the above-described platinum-containing catalyst was added to the reaction mixture. The resulting reaction mixture was heated at reflux for 4 hours and then devolatilized at reduced pressure. The other emulsifiers shown in Table II were similarly prepared.

TABLE 1

| Emulsifier Number | $(CH_3)_3SiO\{(CH_3)(R)SiO\}_y\{(CH_3)(QR')SiO\}_zSi(CH_3)_3$ | | | | | |
|---|---|---|---|---|---|---|
| | R | Y | QR'* | z | Visc., cP | % Q |
| 1. | $C_8H_{17}$ | 64 | A | 1 | 88,000 | 18 |
| 2. | $C_{12}H_{25}$ | 63.5 | A | 1.5 | 68,000 | 20 |
| 3. | $C_{12}H_{25}$ | 63 | A | 2 | — | 25 |
| 4. | $C_{12}H_{25}$ | 62.5 | A | 2.5 | — | 30 |
| 5.** | $C_{12}H_{25}$ | 62 | A | 3 | 246,000 | 34 |
| 6.** | $C_{12}H_{25}$ | 59 | A | 6 | 30,000 | 51 |
| 7. | $C_{14}H_{29}$ | 63 | A | 2 | 212,000 | 23 |
| 8. | $C_{16}H_{33}$ | 62 | A | 3 | wax | 29 |
| 9. | $C_{16}H_{33}$ | 63 | A | 2 | wax | 22 |
| 10. | $C_{18}H_{37}$ | 63 | A | 2 | wax | 20 |
| 11.** | $C_{18}H_{37}$ | 61 | A | 4 | wax | 34 |
| 12. | $C_{12}H_{25}$ | 59 | B | 6 | — | 19 |
| 13. | $C_{12}H_{25}$ | 62 | B | 3 | 5,840 | 10 |

TABLE 1-continued

| Emulsifier Number | $(CH_3)_3SiO\{(CH_3)(R)SiO\}_y\{(CH_3)(QR')SiO\}_zSi(CH_3)_3$ | | | | | |
|---|---|---|---|---|---|---|
| | R | Y | QR'* | z | Visc., cP | % Q |
| 14. | $C_8H_{17}$ | 64 | A | 1 | 51,000 | 18 |
| 15. | $C_{12}H_{25}$ | 64 | A | 1 | 6,000 | 14 |
| 16. | $C_{12}H_{25}$ | 38.7 | C | 1.3 | — | 22 |

*A = $-CH_2CH_2CH_2(OCH_2CH_2)_{24.4}(OCHCH_3CH_2)_{24.4}OH$
B = $-CH_2CH_2CH_2(OCH_2CH_2)_{12.3}OH$
C = $-CH_2CH_2CH_2(OCH_2CH_2)_{19}(OCHCH_3CH_2)_{19}OH$
**Organopolysiloxane not of this invention - for comparison purposes only.

TABLE II

| Emulsifier Number | $(CH_3)_3SiO\{(CH_3)_2SiO\}_x\{(CH_3)(C_{12}H_{25})SiO\}_y\{(CH_3)(QR'^*)SiO\}_zSi(CH_3)_3$ | | | | |
|---|---|---|---|---|---|
| | x | y | z | % Q | Visc., cP |
| 17** | 200 | 45 | 3 | 23 | — |
| 18** | 150 | 45 | 3 | 26 | — |
| 19 | 100 | 46.5 | 1 | 12 | 64,000 |
| 20 | 100 | 45 | 2.5 | 26 | — |
| 21** | 100 | 43 | 4.5 | 39 | — |
| 22 | 60 | 61.3 | 1 | 12 | 69,000 |
| 23 | 30 | 61.3 | 1 | 13 | 70,000 |
| 24 | 30 | 60.8 | 1.5 | 19 | 344,000 |
| 25** | 6.3 | 2 | 2 | 80 | — |

*QR' = $-CH_2CH_2CH_2(OCH_2CH_2)_{24.4}(OCHCH_3CH_2)_{24.4}OH$
**Composition for comparison purposes only Emulsion Preparation—The emulsion compositions that are described in the following examples were prepared by preparing, separately, the indicated oil phase and the indicated aqueous phase and then slowly adding the aqueous phase to the vigorously agitated oil phase, followed by continued agitation of the resulting mixture until it became homogeneous. The agitating means in these examples was an Eppenbach high shear mixer. The indicated emulsifiers are delineated in Table I and II.

EXAMPLE 4

This example illustrates the preparation by the process described above, of a very thick, stiff emulsion of this invention which is useful as a skin cream.

Oil Phase: Mineral oil (8 cst.), 19.6 parts; Emulsifier No. 1, 0.9 parts; Tergitol®15S3 (polyethylene glycol ether of a mixture of $C_{11}$ to $C_{15}$ fatty alcohols with an average of 3 mols of ethylene oxide from Union Carbide Corporation; Danbury, CT.), 0.4 parts.

Aqueous Phase: Water, 78.7 parts; NaCl, 0.4 parts.

After accelerated aging at 40° C. for 7 months the resulting composition showed only minor, but acceptable, signs of emulsion instability.

EXAMPLE 5

The preparation of Example 4 was repeated except that Emulsifier No. 2 was used instead of Emulsifier No. 1. A more stable emulsion was obtained.

EXAMPLE 6

This example illustrates the preparation using the above-described process, of a medium viscosity emulsion composition of this invention which is useful as a skin care lotion.

Oil Phase: Mineral oil (8 cst.), 9.8 parts; Emulsifier No. 1, 1.9 parts; octamethylcyclotetrasiloxane, 11.8 parts; Tergitol®15S3, 1.0 parts.

Aqueous Phase: Water, 73.5 parts; NaCl, 2.0 parts.

The resulting composition was stable and showed no changes when stored at room temperature for 9 months.

EXAMPLES 7 TO 9

These examples illustrate the preparation of skin care lotions of this invention containing a vegetable oil, an animal oil or a high viscosity mineral oil, using the general process described above.

Oil Phase: Mineral oil (12 cst.), 14.0 parts; Emulsifier No. 2, 0.3 parts; sun flower oil (in Ex. 7) or light fraction mink oil (in Ex. 8) or 67 cst. mineral oil (in Ex. 9), 14.3 parts.

Aqueous Phase: Water, 70.7 parts; NaCl, 0.7 parts; for all compositions.

These three compositions were stable and showed only a slight amount of oiling after about 3 weeks at room temperature.

EXAMPLES 10 AND 11

These examples illustrate the preparation of skin care emulsions of this invention containing a plurality of efficacious components for skin care.

Oil Phase: Mineal oil (12 cst.), 14.0 parts; Emulsifier No. 2, 0.3 parts; additional oils*, 14.3 parts.
*Ex. 10: Light fraction mink oil. 13.3 parts; myristyl myristate, 1.0 parts.
*Ex. 11: Petrolatum, 7.6 parts; myristyl myristate, 1.9 parts and $Me_3SiO_{\frac{1}{2}}/PhSiO_{3/2}$ silicone fluid, 4.8 parts.

Aqueous Phase: Water, 61.2 parts; NaCl, 0.6 parts; polyethylene glycol (400 mw), 4.8 parts; N-ethanolacetamide, 4.8 parts; for both compositions.

These emulsions showed no oiling or separation after 24 hours at room temperature and less than 5% oiling and no separation after 20 days at room temperature.

EXAMPLES 12 TO 16

These examples further illustrate the preparation of skin care lotions which contain an efficacious component in the oil phase.

Oil Phase: Mineral oil (8 cst.), 13.7 parts; Emulsifier No. 2, 0.6 parts; light fraction mink oil (in Ex. 12) or octyl hydroxystearate (in Ex. 13) or isopropyl myristate (in Ex. 14) or petrolatum (in Ex. 15) or additional 8 cst. mineral oil (in Ex. 16), 14.3 parts.

Aqueous Phase: Water, 70.7 parts; NaCl, 0.7 parts; for all compositions.

All of these compositions were stable to heat aging at 40° C. for two months. The composition of Example 12 showed some water separation.

EXAMPLES 17 TO 21

These examples illustrate the stabilizing effect of using a higher concentration of Emulsifier No. 2. See Examples 12 to 16 for comparison.

Examples 12 to 16 were repeated except that the amount of Emulsifier No. 2 was increased from 0.6 to 1.0 parts and the amount of mineral oil was decreased, correspondingly, from 13.7 to 13.3 parts. The compositions of Examples 18 to 21 were stable to heat aging at 40° C. for 4½ months. The composition of Example 17 separated.

EXAMPLE 22

This example illustrates various emulsifiers of this invention that are useful for preparing emulsion compositions of this invention.

Eleven hand cream formulations were prepared by the process noted above using the following components.

Oil Phase: Mineral oil (8 cst.), 19.6 parts; Emulsifier Nos. 3, 4, 5, 6, 7, 8, 9, 10, 11, 12 or 13, 0.9 parts.

Aqueous Phase: Water, 78.7 parts; Tergitol®15S3, 0.4 parts; NaCl, 0.4 parts.

The hand cream formulations that were prepared with liquid emulsifiers that contained 30 percent or less by weight polyoxyalkylene groups (Emulsifier Nos. 3, 4, 7, 12 and 13) provided stable formulations. The hand cream formulations that were prepared with emulsifiers having more than 33 percent by weight polyoxyalkylene groups (Emulsifier Nos. 5 and 6) provided agglomerated formulations.

The hand cream formulations that were prepared with solid emulsifiers (Emulsifier Nos. 8, 9, 10 and 11) provided results that are not readily understood at this time. The formulations made with Emulsifier Nos. 10 and 11 appeared to separate a crystalline phase while the formulations made with Emulsifier Nos. 8 and 9 were stable formulations. Apparently the size of the R group in the emulsifier cannot be as large as the octadecyl group.

EXAMPLES 23 TO 36

Fourteen emulsion formulations were made by the above-described general method wherein the aqueous phase consisted of 65 parts of water, 2 parts of NaCl and 1 part of Tergitol®15S3. Thirty-two parts of an oil phase consisting of 2 parts of Emulsifier No. 14 and 30 parts of various emollients were used in these examples and were as follows:

Ex. 23, Klearol® (white mineral oil from Witco-Sonneborn; New York, NY).
Ex. 24, Blandol® (white mineral oil from Witco-Sonneborn; New York, NY).
Ex. 25, Marcol®72 (13 cs. white mineral oil from EXXON Company, U.S.A.; Houston, TX).
Ex. 26, ⅔ Klearol®—⅓ octamethylcyclotetrasiloxane.
Ex. 27, ⅔ Klearol®—⅓ petrolatum.
Ex. 28, ⅓ Klearol®—⅔ petrolatum.
Ex. 29, ⅔ Klearol®—⅓ lanolin oil.
Ex. 30, ½ Klearol®—½ lanolin oil.
Ex. 31, ⅓ Klearol®—⅔ lanolin oil.
Ex. 32, 5/6 Klearol®—1/6 isopropyl myristate.
Ex. 33, ½ Klearol®—½ isopropyl myristate.
Ex. 34, 1/6 Klearol®—5/6 isopropyl myristate.
Ex. 35, 5/6 Klearol®—1/6 paraffin wax.
Ex. 36, ⅔ Klearol®—⅓ paraffin wax.

All formulations, except that of Ex. 31 provided stable emulsions. Furthermore, all stable emulsions, except those of Ex. 34 and 36 were stable to three freeze-thaw cycles.

As a comparison, Example 23 was repeated except that an organopolysiloxane of the art (Emulsifier No. 25, Table II) was used instead of Emulsifier No. 14. The emulsion that was formed was an oil-in-water emulsion, not a water-in-oil emulsion.

EXAMPLE 37

This example illustrates the preparation of a skin care stick formulation of this invention, using the above-described general procedure. The oil phase was heated to 70° C.

Oil Phase: Mineral oil (8 cst.), 20 parts; paraffin wax, 28 parts; Emulsifier No. 14, 2 parts; Tergitol®15S3, 1 part.

Aqueous Phase: Water, 48 parts; NaCl, 1 part.

EXAMPLE 38

This example illustrates the preparaton of a skin care stick formulation of this invention, using the above-described general procedures.

Oil Phase: Mineral oil (8 cst.), 59 parts; Emulsifier No. 14, 3 parts; Tergitol ®15S3, 1 part.

Aqueous Phase: Water, 12 parts; propylene glycol, 4 parts; absolute ethanol, 20.8 parts; sodium stearate, 3.2 parts.

EXAMPLE 39

This example illustrates a compositon of this invention which contains a humectant in the aqueous phase.

Oil Phase: Marcol ®52 (8 cs white mineral oil from EXXON Company, U.S.A.; Houston, TX) 30 parts; Emulsifier No. 14, 2 parts; Tergitol ®15S3, 1 part.

Aqueous Phase: Water, 55 parts; NaCl, 2 parts; 70% aqueous solution of sorbitol, 10 parts.

The resulting emulsion having a particle size of less than 1 micrometer, was placed in a 100° F. oven for aging studies. The emulsion experienced no separation in 20 days.

EXAMPLE 40

This example illustrates a composition of this invention which contains a sun screen in the oil phase.

Oil Phase: Mineral oil (8 cst.), 27.5 parts; Emulsifier No. 14, 2 parts; Tergitol ®15S3, 1 part, Escalol ®507 (octyldimethyl-p-aminobenzoic acid from VanDyk and Company, Inc., Belleville, NJ), 2.5 parts.

Aqueous Phase: Water, 65 parts; NaCl, 2 parts.

EXAMPLE 41

An emulsion composition was prepared with each of Emulsifier Nos. 17 to 21 (Table II).

Oil Phase: Klearol ®, 30 parts; Emulsifiers Nos. 17 to 21, 2 parts; Tergitol ®15S3, 1 part.

Aqueous Phase: Water 65 parts; NaCl, 2 parts.

Those emulsions that were prepared with Emulsifier Nos. 19 and 20 were stable emulsions whereas those prepared with Emulsifier Nos. 17, 18 and 21 were agglomerated emulsions. Emulsifier Nos. 17 and 18 contained too much dimethylsiloxane units whereas Emulsifier No. 21 contained too much hydrophilic portion.

EXAMPLE 42

A stable emulsion composition was prepared with each of Emulsifier Nos. 22 to 24 (Table II).

Oil Phase: Marcol ®52, 30 parts; Emulsifier Nos. 22 to 24, 2 parts; Tergitol ®15S3, 1 part.

Aqueous Phase: Water, 66 parts; NaCl, 1 part.

That which is claimed is:

1. An organopolysiloxane having the formula $$Z(CH_3)_2SiO\{(CH_3)_2SiO\}_x\{(CH_3)(R)SiO\}_y\{(CH_3)(QR')SiO\}_zSi(CH_3)_2Z$$

wherein QR' denotes a polyoxyalkylene radical consisting of a Q portion having the formula 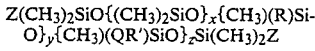 and an R' portion linking the Q portion to a silicon atom, R denotes an alkyl radical having from 6 to 16 carbon atoms, R' denotes an alkylene linking radical, R" denotes a hydrogen atom or a lower alkyl radical, Z denotes a monovalent radical selected from the group consisting of hydrocarbon radicals having from 1 to 5 carbon atoms, QR' radicals and R radicals, there being an average of at least one QR'—radical and an average of at least one R radical per molecule of organopolysiloxane and the average values of x, y, z, p and q being such that $p \geq q$, $p+q$ has a value sufficient to provide a radical weight for Q of from 600 to 3500, $x \leq 3y$, $x+y+z$ has a value of from 30 to 400 and the total weight of Q radicals in the organopolysiloxane does not exceed a value of about ⅓ of the total weight of the organopolysiloxane.

2. An organopolysiloxane according to claim 1 wherein Z denotes the methyl radical, x has a value of zero and $y+z$ has an average value of from about 30 to about 70.

3. An organopolysiloxane according to claim 2 wherein z has a value of from about 1 to about 3 and QR' denotes $-CH_2CH_2CH_2(OCH_2CH_2)_p(OCHCH_3CH_2)_qOH$.

4. An organopolysiloxane according to claim 3 wherein R denotes the dodecyl radical.

5. An organopolysiloxane according to claim 1 wherein x has an average value of from about 1 to about 100, $y+z$ has an average value of from about 30 to about 70 and Z denotes the methyl radical.

6. An organopolysiloxane according to claim 5 wherein z has a value of from about 1 to about 3 and QR' denotes $-CH_2CH_2CH_2(OCH_2CH_2)_p(OCHCH_3CH_2)_qOH$.

7. An organopolysiloxane according to claim 6 wherein R denotes the dodecyl radical.

8. A homogeneous composition comprising (A) an organopolysiloxane having the formula $$Z(CH_3)_2SiO\{(CH_3)_2SiO\}_x\{(CH_3)(R)SiO\}_y\{(CH_3)(QR')SiO\}_ySi(CH_3)_2Z$$

wherein QR' denotes a polyoxyalkylene radical consisting of a Q portion having the formula 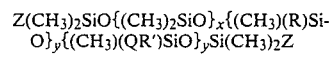 and an R' portion linking the Q portion to a silicon atom, R denotes an alkyl radical having from 6 to 16 carbon atoms, R' denotes an alkylene linking radical, R" denotes a hydrogen atom or a lower alkyl radical, Z denotes a monovalent radical selected from the group consisting of hydrocarbon radicals having from 1 to 5 carbon atoms, QR'—radicals and R radicals, there being an average of at least one QR'—radical and an average of at least one R radical per molecule of organopolysiloxane and the average values of x, y, z, p and q being such that $p \geq q$, $p+q$ has a value sufficient to provide a radical weight of Q of from 600 to 3500, $x \leq 3y$, $x+y+z$ has a value of from 30 to 400 and the total weight of Q radicals in the organopolysiloxane does not exceed a value of about ⅓ of the total weight of the organopolysiloxane, and (B) mineral oil.

9. A composition according to claim 8 wherein Z denotes the methyl radical, x has a value of zero and $y+z$ has an average value of from about 30 to about 70.

10. A composition according to claim 9 wherein z has a value of from about 1 to about 3 and QR' denotes $-CH_2CH_2CH_2(OCH_2CH_2)_p(OCHCH_3CH_2)_qOH$.

11. A composition according to claim 10 wherein R denotes the dodecyl radical.

12. A composition according to claim 8 wherein x has an average value of from about 1 to about 100, y+z has an average value of from about 30 to about 70 and Z denotes the methyl radical.

13. A composition according to claim 12 wherein z has a value of from about 1 to about 3 and QR' denotes —CH$_2$CH$_2$CH$_2$(OCH$_2$CH$_2$)$_p$(OCHCH$_3$CH$_2$)$_q$OH.

14. A composition according to claim 13 wherein R denotes the dodecyl radical.

15. An emulsion composition comprising
(I) a dispersed phase comprising water and a cosmetically acceptable electrolyte dissolved therein,
(II) a cosmetically acceptable continuous phase comprising mineral oil, and
(III) an organopolysiloxane having the formula

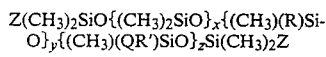

wherein QR' denotes a polyoxyalkylene radical consisting of a Q portion having the formula —(OCH$_2$CH$_2$)$_p$(OCHCH$_3$CH$_2$)$_q$OR'' and an R' portion linking the Q portion to a silicon atom,
R denotes an alkyl radical having from 6 to 16 carbon atoms,
R' denotes an alkylene linking radical,
R'' denotes a hydrogen atom or a lower alkyl radical,
Z denotes a monovalent radical selected from the group consisting of hydrocarbon radicals having from 1 to 5 carbon atoms, QR'—radicals and R radicals, there being an average of at least one QR'—radical and an average of at least one R radical per molecule of organopolysiloxane and the average values of x, y, z, p and q being such that p≧q, p+q has a value sufficient to provide a radical weight for Q of from 600 to 3500, x≦3y, x+y+z has a value of from 30 to 400 and the total weight of Q radicals in the organopolysiloxane does not exceed a value of about ⅓ of the total weight of the organopolysiloxane.

16. An emulsion composition according to claim 15 wherein Z denotes the methyl radical, x has a value of zero and y+z has an average value of from about 30 to about 70.

17. An emulsion composition according to claim 16 wherein z has a value of from about 1 to about 3 and QR' denotes —CH$_2$CH$_2$CH$_2$(OCH$_2$CH$_2$)$_p$(OCHCH$_3$CH$_2$)$_q$OH.

18. An emulsion composition according to claim 17 wherein R denotes the dodecyl radical.

19. An emulsion composition according to claim 15 wherein x has an average value of from about 1 to about 100, y+z has an average value of from about 30 to about 70 and Z denotes the methyl radical.

20. An emulsion composition according to claim 19 wherein z has a value of from about 1 to about 3 and QR' denotes —CH$_2$CH$_2$CH$_2$(OCH$_2$CH$_2$)$_p$(OCHCH$_3$CH$_2$)$_q$OH.

21. An emulsion composition according to claim 20 wherein R denotes the dodecyl radical.

22. An emulsion composition according to claim 18 further comprising a silicon-free nonionic surfactant having an H.L.B. value of up to 10.

23. An emulsion composition according to claim 21 further comprising a silicon-free nonionic siurfactant having an H.L.B. value of up to 10.

* * * * *

UNITED STATES PATENT AND TRADEMARK OFFICE
CERTIFICATE OF CORRECTION

PATENT NO. : 4,532,132
DATED : July 30, 1985
INVENTOR(S) : Joseph W. Keil

Page 1 of 2

It is certified that error appears in the above-identified patent and that said Letters Patent is hereby corrected as shown below:

In column 3, line 13, "p q" should read --$p \geq q$--.

In column 3, line 15, "x 3y" should read --$x \leq 3y$--.

In column 6, line 48, "have" should read --having--.

In column 6, line 49, "...$\}_y\{$ (CH3) (..." should read --...$\}_y\{$ $(CH_3)$ (...--.

In column 9, line 20, insert "as" after the word "such".

In column 9, line 36, "delinated" should read --delineated--.

In column 12, line 11, insert "**" before "Organopolysiloxane".

In column 13, line 21, "Mineal" should read --Mineral--.

In column 15, line 58, "$Z(CH_3)_2SiO\{(CH_3)_2SiO\}_x\{(CH_3)(R)SiO\}_y\{(CH_3)(QR')SiO\}_zSi(CH_3)_2Z$" should read --$Z(CH_3)_2SiO\{(CH_3)_2SiO\}_x\{(CH_3)(R)SiO\}_y\{(CH_3)(QR')SiO\}_zSi(CH_3)_2Z$--.

UNITED STATES PATENT AND TRADEMARK OFFICE
CERTIFICATE OF CORRECTION

PATENT NO. : 4,532,132

DATED : July 30, 1985

INVENTOR(S) : Joseph W. Keil

It is certified that error appears in the above-identified patent and that said Letters Patent is hereby corrected as shown below:

In column 16, line 57 "of Q" should read --for Q--.

In column 18, line 34 "siurfactant" should read --surfactant--.

Signed and Sealed this

Twentieth Day of July, 1993

Attest:

MICHAEL K. KIRK

Attesting Officer

Acting Commissioner of Patents and Trademarks